(12) United States Patent
Cheng et al.

(10) Patent No.: US 11,228,852 B2
(45) Date of Patent: Jan. 18, 2022

(54) REMOTE HEARING TEST SYSTEM AND ASSOCIATED METHODS FOR ESTABLISHING AN AUDITORY PROFILE AND ADJUSTING HEARING AIDS USING SUCH A SYSTEM

(71) Applicant: NEOCUSTIC, Paris (FR)

(72) Inventors: Kwok Kuen Cheng, Saint Germain en Laye (FR); Kwok Wai Cheng, Nogent sur Marne (FR); Laurent Rouvet, Nogent sur Marne (FR); Thierry Didi, Paris (FR)

(73) Assignee: NEOCUSTIC, Paris (FR)

( * ) Notice: Subject to any disclaimer, the term of this patent is extended or adjusted under 35 U.S.C. 154(b) by 0 days.

(21) Appl. No.: 16/649,532

(22) PCT Filed: Sep. 21, 2018

(86) PCT No.: PCT/FR2018/052298
§ 371 (c)(1),
(2) Date: Mar. 20, 2020

(87) PCT Pub. No.: WO2019/058061
PCT Pub. Date: Mar. 28, 2019

(65) Prior Publication Data
US 2020/0260202 A1    Aug. 13, 2020

(30) Foreign Application Priority Data
Sep. 21, 2017   (FR) ........................................ 1758749

(51) Int. Cl.
*H04R 25/00*    (2006.01)
*A61B 1/00*     (2006.01)
(Continued)

(52) U.S. Cl.
CPC ......... *H04R 25/70* (2013.01); *A61B 1/00105* (2013.01); *A61B 1/04* (2013.01);
(Continued)

(58) Field of Classification Search
CPC .... H04R 25/70; H04R 25/554; H04R 25/558; H04R 2225/0216; H04R 2225/04; H04R 2225/55; H04R 2460/01
See application file for complete search history.

(56) References Cited

U.S. PATENT DOCUMENTS

| 2004/0073136 A1 | 4/2004 | Thornton et al. |
| 2005/0059904 A1 | 3/2005 | Chalupper et al. |

(Continued)

FOREIGN PATENT DOCUMENTS

| CN | 101442699 B | 2/2013 |
| WO | 00/42816 A1 | 7/2000 |

OTHER PUBLICATIONS

Bromwich et al., Active Noise Reduction Audiometry: A Prospective Analysis of a New Approach to Noise Management in Audiometric Testing, The Laryngoscope, vol. 118, No. 1, (Jan. 1, 2008), pp. 104-109.

(Continued)

*Primary Examiner* — Brian Ensey
(74) *Attorney, Agent, or Firm* — TraskBritt

(57) ABSTRACT

A hearing test system comprises: a control device for controlling a hearing aid comprising a communication interface arranged to allow two-way communication and software for executing predefined sequences of sounds saved in a memory module of the device in response to an instruction from a control station equipped with remote control software; at least one hearing aid comprising a communication interface arranged to allow two-way communication with the control device, the device comprising a software layer (Continued)

for communication with the hearing aid and being arranged to provide a gateway between the control station and the hearing aid; and means for the sound insulation of the hearing aid.

21 Claims, 1 Drawing Sheet

(51) Int. Cl.
    *A61B 1/04*     (2006.01)
    *A61B 1/227*     (2006.01)
    *A61B 5/03*     (2006.01)
    *A61B 5/12*     (2006.01)
    *A61B 5/00*     (2006.01)

(52) U.S. Cl.
    CPC .............. *A61B 1/227* (2013.01); *A61B 5/036* (2013.01); *A61B 5/125* (2013.01); *A61B 5/4836* (2013.01); *A61B 5/4851* (2013.01); *A61B 5/6817* (2013.01); *A61B 5/7465* (2013.01); *H04R 25/554* (2013.01); *H04R 25/558* (2013.01); *H04R 2225/0216* (2019.05); *H04R 2225/41* (2013.01); *H04R 2225/55* (2013.01); *H04R 2460/01* (2013.01)

(56) References Cited

U.S. PATENT DOCUMENTS

| | | | |
|---|---|---|---|
| 2010/0305469 A1* | 12/2010 | Caballero Catoira | H04R 25/70 600/559 |
| 2014/0194774 A1* | 7/2014 | Gilligan | A61B 5/0022 600/559 |
| 2017/0071534 A1 | 3/2017 | Zhao et al. | |
| 2017/0257713 A1* | 9/2017 | Westermann | H04W 48/18 |

OTHER PUBLICATIONS

International Search Report for International Application No. PCT/FR2018/052298 dated Feb. 12, 2019, 3 pages.
International Written Opinion for International Application No. PCT/FR2018/052298 dated Feb. 12, 2019, 9 pages.

* cited by examiner

REMOTE HEARING TEST SYSTEM AND ASSOCIATED METHODS FOR ESTABLISHING AN AUDITORY PROFILE AND ADJUSTING HEARING AIDS USING SUCH A SYSTEM

CROSS-REFERENCE TO RELATED APPLICATIONS

This application is a national phase entry under 35 U.S.C. § 371 of International Patent Application PCT/FR2018/052298, filed Sep. 21, 2018, designating the United States of America and published as International Patent Publication WO 2019/058061 A1 on Mar. 28, 2019, which claims the benefit under Article 8 of the Patent Cooperation Treaty to French Patent Application Serial No. 1758749, filed Sep. 21, 2017.

TECHNICAL FIELD

The invention relates to the field of audiology, and more particularly to a remote audiometric test system, with the aim of establishing an auditory assessment of a person, as well as remote adjustment of hearing aids on the basis of the auditory assessment established.

BACKGROUND

Conventionally, auditory tests are carried out by a health professional, such as an audioprosthetist, in a suitable medical environment. The auditory tests are generally carried out in three steps. The first step consists in asking the person subject to the auditory test about auditory symptoms, medical history, etc. The second step consists in carrying out an examination of the external auditory canals and eardrums, in order to check the state thereof and to detect possible causes of the hearing loss (otitis, significant amounts of earwax, etc.). The visual examination of the eardrums is carried out using an otoscope. The third step consists in performing an audiogram, and more particularly tone audiometry. This examination aims to identify the auditory thresholds for each ear. This is carried out in a soundproof room or booth, using an audiometer that is capable of producing sounds (pure frequencies) in each ear, in order to measure the auditory threshold. The operator, located outside the booth, controls the audiometer in order to measure the auditory thresholds of each ear, at each frequency range, the maximum thresholds (discomfort threshold) tolerated by the person, and the person's understanding when listening to and recognizing words.

Once the auditory assessment has been carried out, the audioprosthetist determines whether a hearing aid is required and, if so, recommends aural prostheses that should be adjusted so as to be suitable for the person's auditory profile. The adjustment consists in implementing an algorithm that takes account of the audiogram performed, for the person, but also the person's personal data (age, gender, etc.). The parameters obtained are then configured directly on the aural prosthesis. Subsequently, a first step of fine-tuning the adjustment on the basis of person's perception takes place. A second step of fine-tuning takes place on a second occasion, after the prostheses have been working for some days or weeks. The wearer thus returns to the audioprosthetist, who performs a check and, if necessary, further fine-tuning.

However, tests and adjustments of this kind are disadvantageous in that they are relatively expensive and are relatively binding, in terms of time, for the person taking the tests. This is compounded by the fact that people having reduced or poor hearing tend to isolate themselves rather than seek help.

In order to overcome these disadvantages, and to prompt people experiencing hearing difficulties to consult an auditory professional, methods for assessing hearing ability online or by telephone have been developed. These methods have been developed in order that a person can obtain, as an indication, a first assessment of their hearing ability without visiting a medical facility.

However, these methods are not entirely satisfactory because they do not take into account the ambient noise level where the people take the auditory test. Furthermore, the self-assessment tests taken by an individual, online or otherwise, do not allow for calibration of the material used (headphones and amplification), and therefore do not guarantee that a reliable audiogram is achieved. Furthermore, they do not overcome the problem of adjusting the prostheses. Very often, people restrict themselves to the auditory tests, without continuing the process by buying and adjusting auditory prostheses.

The invention aims to overcome the problems by proposing an audiometric measuring system that makes it easier to perform audiograms and to adjust auditory prostheses.

BRIEF SUMMARY

For this purpose, and according to a first aspect, the invention proposes a remote audiometric test system comprising equipment for controlling an aural prosthesis, comprising a communications interface arranged so as to allow for bidirectional communication, software for performing sound sequences that are predefined and recorded in a memory module of the equipment, in response to an instruction originating from a remote control station that is equipped with remote control software, at least one aural prosthesis comprising a communications interface that is arranged so as to allow for bidirectional communication with the control equipment, the equipment comprising a software layer for communication with the aural prosthesis, and being arranged so as to implement a gateway between the control station, which is equipped with software for remote control of the aural prosthesis, and the aural prosthesis, and sound insulation means of the aural prosthesis.

By virtue of this architecture, the auditory tests and the adjustment of the auditory prostheses on the basis of parameters established from auditory tests are carried out remotely, in a simple, rapid and reliable manner.

The sequences of sounds that are predefined and recorded in the memory module of the equipment are advantageously executed by the control equipment in response to a control instruction made directly from the control station. In this case, this is an instantaneous execution of the sound sequences. According to another embodiment, it may also be possible for the sequences of sounds to be executed by the control equipment in response to a control instruction made directly via the equipment, and following reception of an execution authorization instruction originating from the control station. This embodiment involves delayed execution of the sound sequences.

Advantageously, the sound sequences that are predefined and registered in the memory module are also stored in a sub-module of the mobile application that can be downloaded onto the control equipment.

Advantageously, the system comprises image capture means that are arranged together with the prosthesis in order to allow for an image of the inside of the ear when this is provided with the aural prosthesis.

Advantageously, the aural prosthesis comprises a prosthesis body comprising an input transducer for receiving an input signal, and a microcontroller that is designed for controlling the operation of the aural prosthesis 2, the aural prosthesis further comprising an electroacoustic output transducer for producing a perceptible output signal in the form of sound signals, and a signal transmission line for transmitting signals representative of the sound signals to be produced by the electroacoustic output transducer, or produced thereby.

According to a particular embodiment, the electroacoustic output transducer is accommodated in the prosthesis body. In this configuration, the signal transmission line is an acoustic line that guides the sounds produced by the output transducer. According to a variant, the electroacoustic output transducer is positioned at the end of the signal transmission line, the line constituting an electric line in this configuration.

Advantageously, the image capture means are arranged at the end of the signal transmission line.

Advantageously, the signal transmission line is detachably connected to the prosthesis body.

Advantageously, the detachable line is suitable for being connected to another aural prosthesis, it being possible for the communications software layer of the control equipment to be adjusted to the other prosthesis, in order to increase the scope of use of the solution.

Advantageously, the aural prosthesis comprises means for measuring the sound pressure.

Advantageously, the sound insulation means are provided in the form of headphones or, more advantageously, an active headset for eliminating low frequencies.

Advantageously, the audiometric measuring system (remote diagnostics application) is activated in Saas mode, and the data and results of the personalized assessment of the test subject are also stored in Saas mode, in order to ensure security and confidentiality. The mobile application installed on the Smartphone (control equipment) executes the audiometric measuring program, and the data and results are transferred to the system server at the end of the program, for secure storage and in-depth analysis by audiometry professionals.

The invention also relates to a method for creating an auditory assessment for a person, using a remote audiometric test system as described above, the person being provided with aural prostheses in order to carry out an auditory assessment, the prostheses being associated with sound insulation means, wherein the method comprises the steps of:
  transmitting data, relating to sound signals, to the aural prosthesis via the control equipment,
  transmitting the content of vocal responses by the person to the control station, via the control equipment,
  continuously measuring the sound pressure within the sound insulation equipment, and transmitting data to the control station, via the control equipment.

Advantageously, the data relating to sound signals are transmitted to the aural prosthesis either from the control station, via the control equipment, or by the control equipment in response to a transmission authorization originating from the control station.

The invention also relates to a method for adjusting an aural prosthesis comprising a bidirectional communications interface, using a remote audiometric test system as described above, the method comprising a step of transmission of adjustment data to the prosthesis from an auditory profile of the person established from the control station, by means of the control equipment.

The invention also relates to a method for stimulating a person's hearing ability, using a remote audiometric test system as described above, proceeding from an auditory assessment created for the person in accordance with the method for creating an auditory assessment of a person, as described above.

BRIEF DESCRIPTION OF THE DRAWINGS

Further objects and advantages of the invention will become clear from the following description, given with reference to the accompanying drawings, in which.

DETAILED DESCRIPTION

Figure 1:
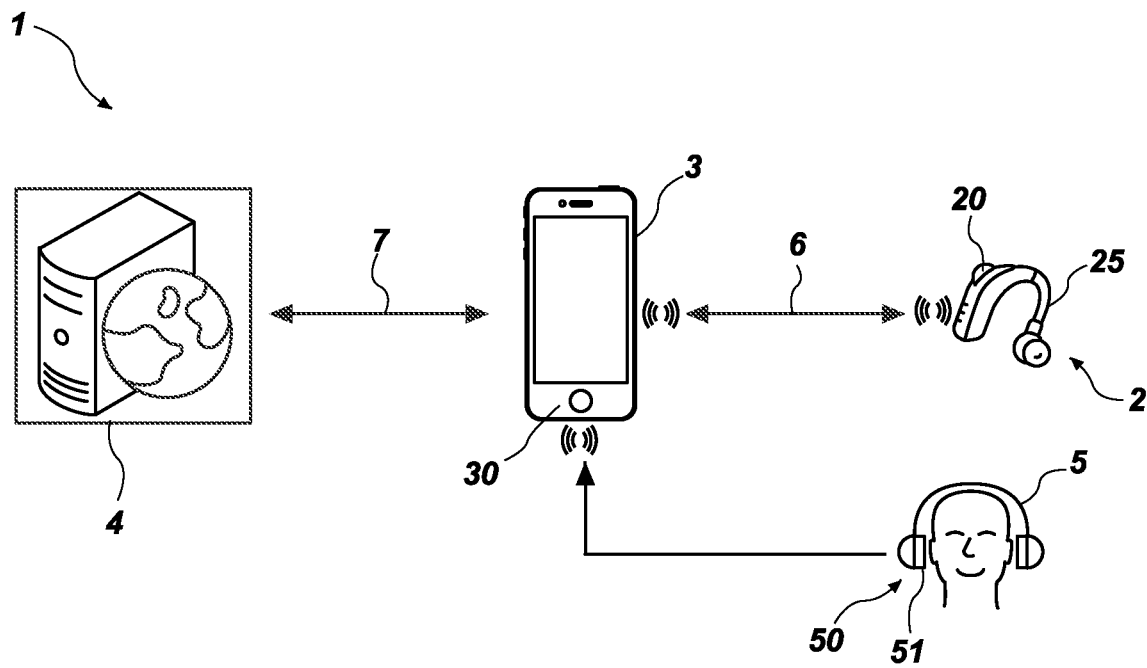
FIG. 1 is a synoptic view of a remote audiometric test system.

A remote audiometric test system 1 is described with reference to FIG. 1. As will be understood in the following, the remote audiometric test system 1 also makes it possible to perform remote parameterization of one or more aural prosthesis/prostheses, on the basis of an auditory profile created using the audiometric measures set out.

The audiometric test system 1 comprises two aural prostheses 2 (one prosthesis for the right ear, and one prosthesis for the left ear, but only one prosthesis is shown), control equipment 3 of the aural prosthesis 2, and a remote control station 4 comprising a patient database and remote control software. The aural prosthesis 2 is connected to the control equipment 3 via a wireless connection of the Bluetooth type, which is itself connected to the control station 4 via a communications network 7 of the Internet type and a mobile telecommunications module.

The control equipment 3, which is preferably mobile and is shown in FIG. 1, is a Smartphone. This is an embodiment; any other communications or terminal equipment, mobile or not, such as a digital tablet or the like, constitutes control equipment 3 according to the present disclosure. The features described in the following, with respect to the Smartphone, therefore also apply, by extension, to any type of communications or terminal equipment other than a Smartphone that is capable of being implemented according to the present disclosure. As will be seen below, the control equipment 3 (Smartphone) serves as a communications gateway, comprising means for controlling access to the prostheses, between the control station 4, which may be the remote terminal of the audioprosthetist, and the auditory prostheses worn by the person. It comprises a proprietary application that functions as a communications relay between the control station 4 and the prostheses, comprising access control to the prostheses, and designed to configure each of the aural prostheses 2 on the basis of instructions received from the control station 4.

Figure 2:
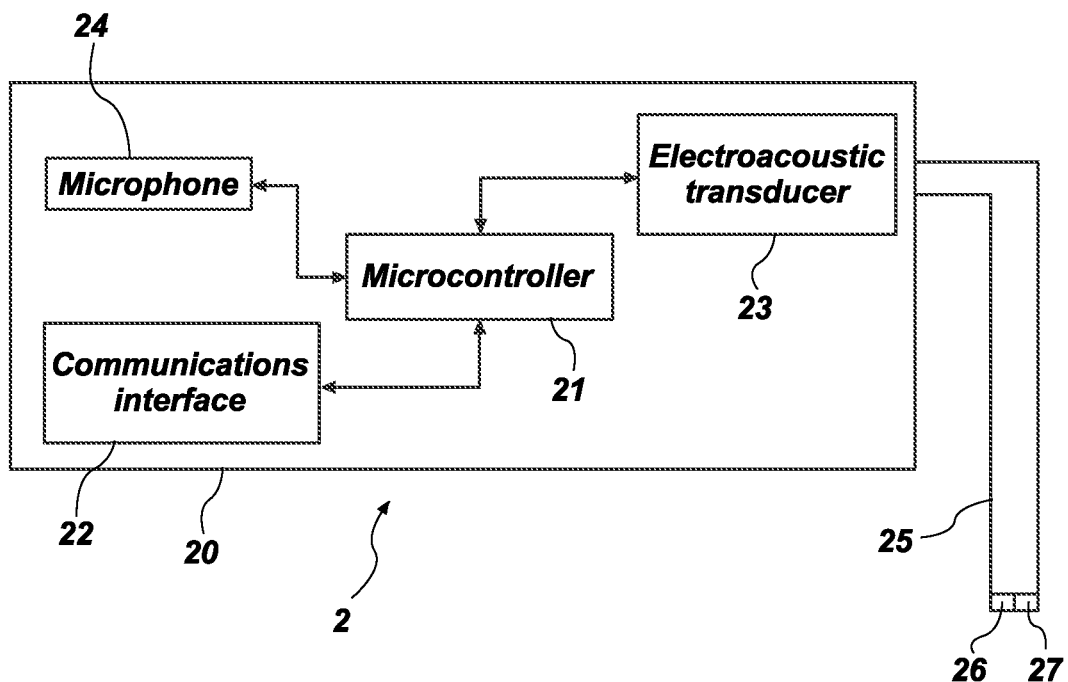
FIG. 2 is a block diagram of the aural prosthesis implemented in the system of FIG. 1.

The aural prosthesis 2, the block diagram of which is shown in FIG. 2, is an aural prosthesis of the BTE (Behind the Ear) format type, connected to the contour of the ear. It could, of course, be a prosthesis of the RIC (Received in Canal) format, or ITE (In the Ear) format, or any other prosthesis format available or to come in the future, without departing from the scope of the present disclosure.

According to the BTE format, the aural prosthesis 2 comprises a prosthesis body 20 comprising, other than an input transducer for receiving an input sound signal (not shown), a microcontroller 21 designed for controlling the operation of the aural prosthesis 2, a wireless communications interface 22 (Bluetooth) that is designed to allow for bidirectional communication with the control equipment 3, which also comprises a wireless communications interface (Bluetooth).

The prosthesis body 20 further comprises an electroacoustic output transducer 23 (loudspeaker) that is designed to produce sound signals at pure frequencies, in accordance with sound sequences that are predefined and recorded in a memory module of the control equipment 3. Designed in this manner, the aural prosthesis 2 functions, together with the control equipment 3, as an audiometer.

The prosthesis body 20 also comprises a measurement means, such as a microphone 24, for measuring the sound level of the environment in which the auditory prostheses are located. The sound level is measured in different frequencies of the sound spectrum to which human ears are sensitive (frequencies of between 16 Hz and 8000 Hz). As will be seen below, the measurements made by the microphone 24 are transmitted to the control station 4 via the control equipment 3, in order to check whether the noise level surrounding the prosthesis is lower than a limit threshold above which the sound level is considered unacceptable for carrying out an auditory test.

The prosthesis body 20 is provided with an acoustic line 25 that makes it possible to guide sounds produced by the loudspeaker to the inside of the ear in which the end of the acoustic line is placed. In the case of a prosthesis of the RIC format, the electroacoustic output transducer is integrated in the tip of the prosthesis that is intended to enter into the auditory canal of the person wearing the aural prosthesis. In this case, the line connecting the output transducer to the electronic part contained in the body of the housing is not an acoustic line, but an electric line. In the case of a prosthesis of the ITE format, the electroacoustic output transducer is completely integrated in the prosthesis that is inserted into the auditory canal, following a customized impression; this is an "invisible" prosthesis.

Advantageously, the audiometric test system 1 comprises image capture means. In the embodiment shown, the image capture means comprise a camera 26 and associated illumination means 27, which are integrated in the line 25 of the aural prosthesis 2. This thus allows the operator to view the patient's eardrums from the control station 4, via the Smartphone 3 or other external equipment to which the camera is connected. As shown in FIG. 2, the camera is positioned at the end of the line 25. The same applies for the illumination means. It is also possible, according to a variant, to equip the outside wall of the line 25 with one or more optical fibers for guiding the light, originating from a light source located in the region of the prosthesis body 20 or so as to be remote therefrom, the optical fiber(s) advantageously extending as far as the region of the proximal end of the line (end further from the prosthesis body 20). It may also be possible to position the camera at the end of the optical fiber opposite the end leading into the region of the proximal end of the line.

Advantageously, the line 25 is detachably connected to the prosthesis body 20. This thus makes it possible to swap the lines, thus making the aural prosthesis 2 flexible. In particular, this makes it possible to change from an instrumented prosthesis, referred to as a test prosthesis, making it possible to implement the audiometric measures with the aim of creating an auditory assessment of the person, to a hearing aid prosthesis, strictly speaking. In this latter configuration, the acoustic line 25 mounted on the prosthesis body would be a simple acoustic line without a camera or associated lighting means.

The test system 1 further comprises sound insulation means that are designed for providing insulation, from the sound perspective of the aural prosthesis 2, in noisy environments. Advantageously, the sound insulation means are in the form of headphones 5 having a layer of insulating material 51 over the entire perimeter of each of the earpieces 50 thereof (FIG. 1). Advantageously, it may be possible for the headphones 5 to be active headphones, making it possible to improve the sound insulation of low frequencies. In the present disclosure, low frequency is intended to mean frequencies of less than or equal to 1000 Hz. It is thus advantageously possible to use ANR technology, such as headphones of the NoiseMaster™ range. As will be seen below, the sound insulation means are used during the auditory tests, during production of the assessment. It is of course obvious that the present disclosure is not limited to this type of equipment, and that any other item of equipment that makes it possible to insulate the patient from ambient noise can be implemented, without departing from the scope of the present disclosure.

In order to improve the sound insulation in the region of the aural prostheses 2, the acoustic line 25 may comprise an, advantageously single-use, foam head at the end.

The auditory assessment and the parameterization of the aural prostheses 2 on the basis of the auditory assessment, are carried out in the following manner.

First, the hearing profile of the person is established. In order to achieve this, the person is provided with the aural prostheses 2 and the sound isolation headphones 5, in order to place the prostheses in a suitable environment, i.e., in an environment that is limited with respect to ambient noise.

From the control station 4, the operator sends the instructions to the Smartphone 3 in order to activate the application and the associated program for creating the hearing profile. Upon receipt of the instructions, the Smartphone 3 transmits, via Bluetooth, the data recorded in the memory module and relating to the sequences of sound signals investigated for carrying out the auditory test, to each of the aural prostheses 2, in accordance with the instructions given by the operator. The data are transmitted simultaneously or in succession, depending on the program launched. The data received by the aural prostheses 2 are then processed and transmitted to the transducer 23, which reproduces the sequences of sound signals inside the auditory canal of the wearer of the prosthesis, via the acoustic line 25 of the prosthesis. The vocal responses of the wearer of the prosthesis, upon reception of the sound signals, are recovered by the microphone 30 of the Smartphone, in order to be transmitted to the remote control station 4. The wearer's responses are recorded in a memory module of the remote control station 4.

At the same time as the transmission of the sound signals to be produced by the aural prostheses 2, the sound level present inside the headphones 5 (in the example shown, inside each of the earpieces of the headphones) is measured and transmitted in real time, via Bluetooth, to the Smartphone 3, which transmits this via the Internet to the remote control station 4. The data relating to the sound level, which data are measured during the auditory test, are stored in the memory module of the control station 4.

Prior to launching the auditory test, the operator can check the inside of the ears, and, in particular, check that these do not contain elements likely to cause hearing loss, such as the presence of a plug of earwax. In order to achieve this, the operator remotely activates the camera 26 provided at the end of the acoustic line 25 of the aural prostheses 2, via the Smartphone 3, and checks the inside of the ear in real time. This step is optional.

The audioprosthetist creates the patient's auditory assessment on the basis of the patient's responses received from the aural prostheses 2 via the Smartphone 3.

Subsequently, the aural prostheses 2 intended to be worn are adjusted on the basis of the created auditory assessment. The adjustments are transmitted to each of the aural prostheses 2 via the Smartphone 3. More specifically, and as for the performance of the auditory test, the adjustments to be made to the aural prosthesis/prostheses 2 are transmitted to the dedicated application downloaded to the Smartphone, which functions as a communications gateway between the remote control station 4 to which the operator connects, and the aural prostheses 2 of the wearer. The application configures the aural prosthesis or the two aural prostheses on the basis of the received adjustment data.

In the embodiment that has just been described, the auditory assessment is performed following a command instruction originating directly from the audioprosthetist, from the control station. It may also be possible, according to a variant, that a remote diagnosis is performed following a command instruction of the auditory assessment, directly from the Smartphone. In this case, the wearer of the prosthesis launches the dedicated application for performing the diagnosis, previously installed on the Smartphone, which runs the sound signal sequences for each of the prostheses. The application is launched following reception, if applicable, of an execution authorization originating from the control station. The vocal or tactile responses of the wearer, in response to the sound signals emitted, are then recorded and then processed via the dedicated Smartphone application. Following processing of the responses of the wearer of the prostheses, the hearing ability of each of the ears is confirmed, and a preliminary auditory assessment for the wearer is created. The results are then transmitted to the control station in order to establish a complete auditory assessment that is confirmed by the audioprosthetist.

Advantageously, the application installed on the Smartphone is configured so as to allow the wearer of the prostheses to intervene in the general amplification of preprogramed customized adjustments, referred to as final customized adjustments. The wearer can thus intervene, in particular, with regard to the sound volume emitted by the prostheses, and to modulate this so as to be lower or higher pitched. The wearer can also specify a use environment from a group of specified environments (television, noisy restaurant, street, conversation in a private room, etc.). The use environment may be selected either manually by the wearer of the prostheses, or automatically by means of an artificial intelligence (AI) algorithm.

The use data and the use environments selected (amplified sound, selected environment, etc.) are then collected and transmitted into a database of personal data of the patient, stored in the control station and made available to the audioprosthetist for analyses and optimization of the subsequent final customized adjustments.

It may also be possible for the audiometric test system described above to be used for stimulating the hearing ability of a wearer of the prostheses (auditory re-education). In order to achieve this, the Smartphone 3 (and more generally the control equipment) comprises an application that is dedicated to this use. In order to activate the auditory stimulation, the wearer launches the dedicated application, which senses a sequence of programmed signals in order to stimulate the attention of the wearer, taking account of the level of hearing impairment. The application then records the reactions of the wearer or the actions of the person (vocal or tactile responses) while the program is run. The results obtained are then transmitted by the application to the control station in order to be compared with the results previously memorized in stimulation programs, and to thus make it possible to measure the progress in understanding achieved by the wearer. On the basis of the progress identified, a new stimulation program, taking into account the auditory progress of the wearer, is created, in order to continue with the progression in the understanding of words and sounds transmitted to the patient via his Smartphone.

Advantageously, the predefined sequences of sounds within the scope of the auditory assessment, those predefined within the context of auditory re-education, and the AI part within the context of selecting the use environment constitute independent sub-modules that are accommodated in the same application, it being possible for each of the sub-modules to be downloaded to the Smartphone (and more generally to the control equipment) independently of one another.

The present disclosure is described above by way of example. It will be understood that a person skilled in the art is able to implement different variants of the present disclosure, without in any way departing from the scope of the present disclosure.

The invention claimed is:

1. A remote audiometric test system, comprising:
   at least one aural prosthesis;
   control equipment for controlling the at least one aural prosthesis, each of the at least one aural prosthesis and the control equipment including a respective communication interface for enabling bidirectional communication between the control equipment and the at least one aural prosthesis; and
   a sound insulation device for insulating the aural prosthesis to external sound;
   wherein the control equipment is configured under control of a computer program to cause the at least one aural prosthesis to execute sound sequences recorded in a memory module of the control equipment in response to an instruction originating from a remote control station, and to implement a gateway between the remote control station and the at least one aural prosthesis to enable remote control of the at least one aural prosthesis by the remote control station; and
   wherein the control equipment is further configured under control of the computer program to employ an artificial intelligence algorithm and automatically select a use environment from a group of specified use environments and adjust one or more operational parameters of the at least one aural prosthesis on the basis of the automatically selected use environment.

2. The system of claim 1, wherein the at least one aural prosthesis comprises a camera configured to acquire an image of an inside of an ear when the at least one aural prosthesis is positioned on the ear.

3. The system of claim 2, wherein the at least one aural prosthesis comprises a prosthesis body comprising an input transducer for receiving an input signal, and a microcontroller for controlling an operation of the at least one aural prosthesis, the at least one aural prosthesis further comprising an electroacoustic output transducer for producing a perceptible output sound signal, and a signal transmission line for transmitting signals representative of the sound to be produced by the electroacoustic output transducer.

4. The system of claim 3, wherein the camera is located at an end of the signal transmission line.

5. The system of claim 3, wherein the signal transmission line is detachably connected to the prosthesis body.

6. The system of claim 1, wherein the at least one aural prosthesis comprises a sound pressure level sensor.

7. The system of claim 1, wherein the sound insulation device comprises headphones.

8. The system of claim 7, wherein the headphones comprise active noise reduction headphones.

9. A method for performing an auditory assessment for a person, comprising:
- positioning at least one aural prosthesis on an ear of the person;
- using a sound insulation device to insulate the at least one aural prosthesis and the ear of the person from external sound;
- transmitting data relating to sound signals to the at least one aural prosthesis from control equipment for controlling the at least one aural prosthesis, each of the at least one aural prosthesis and the control equipment including a respective communication interface for enabling bidirectional communication between the control equipment and the at least one aural prosthesis;
- transmitting content of vocal responses by the person to a remote control station via the control equipment;
- continuously measuring sound pressure levels within the sound insulation device, and transmitting data relating to the measured sound pressure levels to the remote control station via the control equipment;
- executing an artificial intelligence algorithm using the control equipment and automatically selecting a use environment from a group of specified use environments via the artificial intelligence algorithm; and
- adjusting one or more operational parameters of the at least one aural prosthesis on the basis of the automatically selected use environment.

10. The method of claim 9, wherein the data relating to the sequences of sound signals are transmitted from the remote control station to the at least one aural prosthesis via the control equipment.

11. The method of claim 9, wherein the data relating to the sequences of sound signals are transmitted to the at least one aural prosthesis from the control equipment, in response to a transmission authorization from the remote control station.

12. The method of claim 9, further comprising adjusting an operational parameter of the at least one aural prosthesis by transmitting adjustment data to the at least one aural prosthesis from the remote control station via the control equipment.

13. A system for adjusting at least one aural prosthesis using a remote computer, comprising:
- at least one aural prosthesis;
- a mobile computer device, each of the at least one aural prosthesis and the mobile computer device including a respective communication interface for enabling bidirectional communication between the mobile computer device and the at least one aural prosthesis; and
- a remote computer located remotely relative to the at least one aural prosthesis and the mobile computer device;
- wherein the mobile computer device is configured under control of a computer program to cause the at least one aural prosthesis to execute sound sequences recorded in a memory module of the mobile computer device in response to an instruction originating from the remote computer, and to implement a communication gateway between the remote computer and the at least one aural prosthesis to enable remote control of the at least one aural prosthesis by the remote computer; and
- wherein the mobile computer device is further configured under control of the computer program to employ an artificial intelligence algorithm and automatically select a use environment from a group of specified use environments and adjust one or more operational parameters of the at least one aural prosthesis on the basis of the automatically selected use environment.

14. The system of claim 13, wherein the mobile computer device is further configured under control of the computer program to record voice responses of a person wearing the at least one aural prosthesis, and transmit data relating to the recorded voice responses to the remote computer.

15. The system of claim 13, wherein the at least one aural prosthesis comprises a camera configured to acquire an image of an inside of an ear when the at least one aural prosthesis is positioned on the ear.

16. The system of claim 15, wherein the camera is located at an end of a signal transmission line.

17. The system of claim 16, wherein the signal transmission line is detachably connected to a main body of the at least one aural prosthesis.

18. The system of claim 13, wherein the at least one aural prosthesis comprises a sound pressure level sensor.

19. The system of claim 13, further comprising a sound insulation device configured to insulate the at least one aural prosthesis from external noise while adjusting the at least one aural prosthesis during operation of the system.

20. The system of claim 13, wherein the at least one aural prosthesis comprises active noise reduction headphones.

21. The system of claim 13, wherein the mobile computer device is further configured under control of the computer program to optimize at least one operational parameter of the at least one aural prosthesis using the automatically selected use environment and at least some use data collected and transmitted to a database of personal data stored in memory of the mobile computer device.

* * * * *